United States Patent [19]

Verrier

[11] Patent Number: 5,269,326
[45] Date of Patent: Dec. 14, 1993

[54] METHOD FOR TRANSVENOUSLY ACCESSING THE PERICARDIAL SPACE VIA THE RIGHT AURICLE FOR MEDICAL PROCEDURES

[75] Inventor: Richard L. Verrier, Bethesda, Md.

[73] Assignee: Georgetown University, Washington, D.C.

[21] Appl. No.: 782,310

[22] Filed: Oct. 24, 1991

[51] Int. Cl.$^5$ .............................................. A61B 5/00
[52] U.S. Cl. .................... 128/642; 128/656; 128/768; 128/696; 607/120; 607/126; 604/53
[58] Field of Search ...................... 604/22, 27, 28, 52, 604/53, 93, 96, 264, 272, 280–283; 606/185; 128/642, 654, 768

[56] References Cited

U.S. PATENT DOCUMENTS

| | | | |
|---|---|---|---|
| 3,630,207 | 12/1971 | Kahn et al. | 604/282 |
| 3,680,544 | 8/1972 | Shinnick et al. | 128/768 |
| 4,003,379 | 1/1977 | Ellinwood, Jr. | |
| 4,146,029 | 3/1979 | Ellinwood, Jr. | |
| 4,173,981 | 11/1979 | Mortensen | 604/282 |
| 4,181,123 | 1/1980 | Crosby | |
| 4,292,976 | 10/1981 | Banka | 128/656 |
| 4,319,562 | 3/1982 | Crosby | |
| 4,619,247 | 10/1986 | Inoue et al. | 604/96 |
| 4,699,147 | 10/1987 | Chilson et al. | 128/642 |
| 4,717,387 | 1/1988 | Inoue et al. | 604/264 |
| 4,769,016 | 9/1988 | LaBianca | 604/280 |
| 4,884,567 | 12/1989 | Elliott et al. | |
| 4,946,457 | 8/1990 | Elliott | |
| 4,961,731 | 10/1990 | Bodicky et al. | 604/280 |
| 4,991,578 | 2/1991 | Cohen | |
| 4,991,603 | 2/1991 | Cohen et al. | |
| 4,998,975 | 3/1991 | Cohen et al. | |
| 5,033,477 | 7/1991 | Chin et al. | 128/785 |
| 5,092,848 | 3/1992 | DeClutis | 604/272 |
| 5,137,510 | 8/1992 | Van Deripe | 604/28 |
| 5,147,336 | 9/1992 | Wendell et al. | 604/283 |

OTHER PUBLICATIONS

Richard L. Verrier et al., "Prevention of Ventricular Fibrillation by Use of Low-Intensity Electrical Stimuli", *Reprinted from Annals of the New York Academy of Sciences*, 1982, pp. 355–370.

Richard L. Verrier et al., "Protective Zone and the Determination of Vulnerability to Ventricular Fibrillation", *The American Physiology Society*, 1978, Order No. 0363-6135/78/0000-0000, pp. H592–H596.

Boaz Avitall et al., "Iontophoretic Delivery of Dobutamine: An Effective Method to Increase Contractility of Non-Transmural Infarcts" *JACC*, vol. 17, No. 2, Feb., 1991, p. 27A.

Boaz Avitall et al., "Iontophoretic Transport of Procainamide and D-Sotalol Into Arrhythmogenic Myocardium: Efficacy In Ventricular Tachycardia Suppression", *JACC*, vol. 17, No. 2, Feb., 1991, p. 39A.

*Primary Examiner*—William E. Kamm
*Attorney, Agent, or Firm*—Sterne, Kessler, Goldstein & Fox

[57] ABSTRACT

A method for placing various types of catheters into the pericardial space takes advantage of the fact that the right auricle is a thin-walled, low-pressure structure which can be readily penetrated without damaging the pericardium or the epicardium. The method avoids surgical trauma and the risks of general anesthesia and infection. A catheter is guided downstream through one of the venae cavae to the right atrium. Once inside the right atrium, the catheter is passed into the right auricle. The wall at the apex of the right auricle is then pierced to gain access to the pericardial space. The method can be used, for example, to provide electrical stimuli to the heart (e.g., for pacing, cardioversion, and defibrillation), to pick-up an ECG signal, to deliver pharmacologic agents to the heart, to improve vascularization, to remove pericardial fluid for analysis or pericardiocentesis, or to inject a radio-labelled or echo-sensitive dye into the pericardial space for precision fluid imaging.

13 Claims, 5 Drawing Sheets

| Examples of Medical Procedures which may be Performed on the Heart via the Pericardial Space (step 510) |
|---|
| 1. A pharmacologic agent may be introduced into the pericardial space via a catheter. |
| 2. Electrical energy (e.g., an ECG) may be detected with an electrode. |
| 3. Electrical stimuli may be delivered to the heart via an electrode. |
| 4. A fluid (e.g., pericardial fluid) may be withdrawn from the pericardial space. |
| 5. A sample of the pericardial fluid may be withdrawn and analyzed for diagnostic purposes. |
| 6. An imaging fluid may be injected into the pericardial space for fluid imaging of the heart. |
| 7. Electrical energy may be delivered to the heart muscle with an electrode to iontophoretically enhance the delivery of a pharmacologic agent. |

FIG. 6

METHOD FOR TRANSVENOUSLY ACCESSING THE PERICARDIAL SPACE VIA THE RIGHT AURICLE FOR MEDICAL PROCEDURES

STATEMENT AS TO RIGHTS TO INVENTIONS MADE UNDER FEDERALLY-SPONSORED RESEARCH AND DEVELOPMENT

Part of the work performed during development of this invention utilized U.S. Government funds. The U.S. Government has certain rights in this invention.

BACKGROUND OF THE INVENTION

1. Field of the Invention

The invention relates to the field of cardiology. More specifically, the invention relates to a method for diagnosing and treating the heart by facilitating access to the pericardial space.

2. Background Art

An important problem in cardiology is the provision of a safe method for diagnosing and treating the heart selectively and without thoracotomy (open chest surgery). Diagnosis or treatment may be pharmacologic or electrophysiologic. For example, in order to deliver electrical stimuli directly to the heart for the purpose of cardioversion or defibrillation, patients often undergo a thoracotomy under general anesthesia for attachment of a "patch" electrode to the epicardial surface. This procedure requires an extensive incision of the pericardium. The "patch" electrode provides a large electrode surface area in contact with the heart so that a sufficient mass of cardiac tissue may be depolarized. Thoracotomy creates the additional complication of wound healing.

It is desirable to provide a method for placing the defibrillation/cardioversion electrodes in contact with the heart muscle without thoracotomy. U.S. Pat. Nos. 4,181,123 and 4,319,562 to Crosby, and 5,033,477 to Chin et al. disclose methods for placing electrodes in contact with the heart muscles from within the pericardial space without the need for thoracotomy. Access to the pericardial space is gained via a sub-xiphoid route. This involves penetrating the chest wall below the xiphoid process.

The sub-xiphoid route has several disadvantages. First, because the pericardial sac which surrounds the heart is a tight-fitting fibrous membrane, the pericardial space is so small that it is difficult to penetrate the sac without also puncturing, and thereby, damaging the heart itself. Second, accessing the heart via the sub-xiphoid route entails a high risk of infection. These are likely to account for the failure of these methods to be adopted into common clinical practice.

In fact, the sub-xiphoid route is presently used almost solely for pericardiocentesis, a process for the aspiration of excess fluid from the pericardial sac. Pericardiocentesis is normally performed to treat cardiac tamponade, a build-up of excess fluid in the pericardial sac. The excess fluid distends the pericardial sac away from the heart such that the risk of puncturing the heart is reduced, but the risk of infection remains high.

U.S. Pat. Nos. 4,884,567 to Elliott et al., 4,946,457 to Elliott, and 4,998,975 to Cohen et al. disclose methods for transvenous implantation of electrodes into the pericardial space. A catheter is introduced through a vein to the right atrium where the lateral atrial wall is penetrated in order to introduce electrodes into the pericardial space. A major problem encountered by these methods is how to penetrate the lateral atrial wall without also puncturing the tight-fitting pericardium.

The methods of these patents attempt to solve this problem through several elaborate schemes. One scheme involves using complex catheters to attach to the lateral atrial wall and to pull it back away from the pericardium prior to penetrating the wall in order to avoid puncturing the pericardium. Another approach involves injecting a fluid into the pericardial space to distend the pericardium away from the lateral atrial wall prior to penetrating the wall.

U.S. Pat. No. 4,991,578 to Cohen discloses a method for implanting epicardial defibrillation electrodes into the pericardial space via the sub-xiphoid route. As discussed above, it is difficult to penetrate the pericardial sac via the sub-xiphoid route without also puncturing, and thereby damaging, the heart itself. Like the method discussed directly above, the '578 patent discloses injecting a fluid into the pericardial space or attaching and pulling on a catheter to distend the pericardial sac away from the heart.

U.S. Pat. No. 4,991,603 to Cohen et al. discloses a method for implanting defibrillation electrodes in contact with epicardial or pericardial tissue from an inferior vena cava access site. A hole is made in the inferior vena cava and a catheter is transvenously inserted into the inferior vena cava and out through the hole into the chest cavity adjacent the heart. The catheter then pierces the pericardial sac to access the pericardial space. The risk of damaging the heart muscle remains high with this method.

Because each of these known methods is intrinsically cumbersome and hazardous, they have not gained widespread use. What is needed is a simpler, safer, and more effective way of accessing the pericardial space for delivery of electricity directly to the heart muscle.

In addition to providing a convenient location for placement of electrodes, the confines of the pericardial sac provide an excellent opportunity to isolate the heart for treatment and diagnosis. By introducing pharmacologic agents directly into the pericardial sac, high cardiac drug concentrations can be achieved without spillage or systemic distribution to other organs or tissues.

The pericardial sac has been used for containment of pharmacologic agents for a number of years in experimental settings, but delivery has heretofore required open chest surgery to access the pericardial space. U.S. Pat. Nos. 4,003,379 and 4,146,029 to Ellinwood disclose an implantable medication dispensing apparatus which is adapted to dispense drugs to the pericardial sac over a long period of time, for example, to prevent arrhythmias. The Ellinwood patents, however, do not teach a method for routing the drugs into the pericardial sac.

The present invention seeks to improve upon the conventional methods of diagnosing and treating the heart via the pericardial space by providing a method for safely and reliably introducing a catheter and/or electrodes into the pericardial space.

SUMMARY OF THE INVENTION

The invention is a method for the nonsurgical placement of various types of catheters into the pericardial space. The method takes advantage of the fact that the right auricle is a thin-walled, low-pressure structure which can be readily penetrated without damaging the pericardium or the epicardium.

The method involves guiding a catheter downstream through one of the venae cavae to the right atrium. Once inside the right atrium, the catheter is passed into the right auricle. The wall at the apex of the right auricle is then pierced with the catheter, and the catheter is advanced into the pericardial space.

The right auricle lies tangential to and between the pericardium and the epicardium such that a catheter steered into the right auricle via the right atrium will be positioned substantially in parallel with the wall of the pericardium such that when the wall of the right auricle is pierced by the catheter, it is done substantially without risk of damaging either the pericardium or the epicardium.

The method can be used, for example, to provide electrical stimuli to the heart (e.g., for pacing, cardioversion, and defibrillation), to sense ECG signals, to deliver pharmacologic agents to the heart, to remove pericardial fluid (e.g., for analysis or pericardiocentesis), or to inject a radio-labelled or echo-sensitive dye into the pericardial space for precision fluid imaging.

DESCRIPTION OF THE PREFERRED EMBODIMENT

The invention is a method for treating and diagnosing the heart selectively via the pericardial space without surgical trauma or the risks of general anesthesia and infection. Neither thoracic nor sub-xiphoid access is utilized, and there is minimal risk of damage to the pericardium or the epicardium. The method takes advantage of the fact that the pericardial sac isolates the heart such that it may be treated or diagnosed separately from the remainder of the body. Because of its feasibility and safety, this method could lead to common usage by cardiologists and open up the field of pericardial therapy. Heretofore there has been reluctance to pursue this field because of the hazardous and cumbersome nature of existing techniques for accessing the pericardial space.

Figure 1:
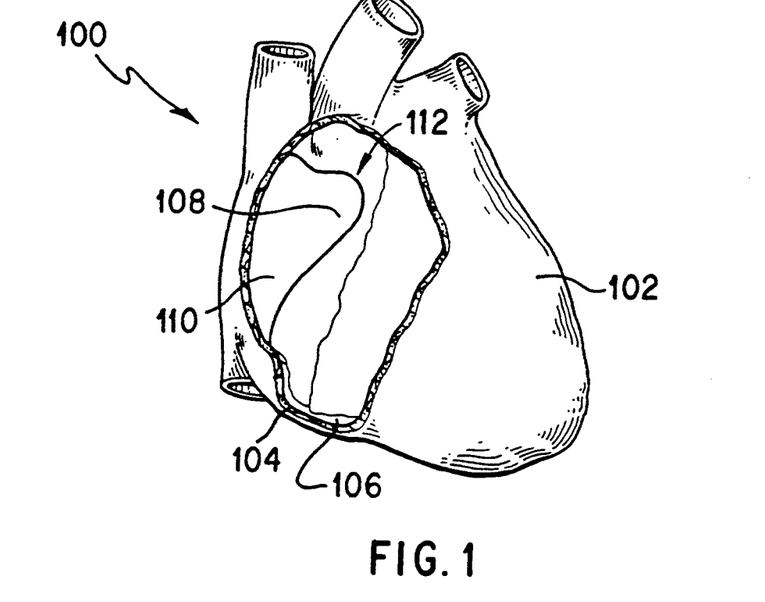
FIG. 1 is a simplified diagram of a human heart with a portion of pericardium 102 cut away.

FIG. 1 shows a heart 100 isolated from the body. The pericardium or pericardial sac 102 encases the cardiac muscle (i.e., epicardium, myocardium and endocardium). A portion of pericardium 102 has been removed to show the underlying cardiac muscle. The cut edge of pericardium 102 is designated 104. The small space which is present between the heart muscle and pericardium 102 is known as the pericardial space 106.

The inventor has discovered that the right atrial appendage or right auricle 108 is an ideal site for entry into the pericardial space. Right auricle 108 lies tangential to and between pericardium 102 and the epicardium. A catheter guided into right auricle 108 via right atrium 110 will automatically be positioned substantially in parallel with the wall of pericardium 102 such that when the wall of right auricle 108 is pierced by a catheter, it is done substantially without risk of damaging either pericardium 102 or the epicardium.

By contrast, the conventional methods penetrate the lateral atrial wall perpendicular to the pericardium so that the risk of damaging the pericardium is high.

Right auricle 108 is a thin-walled, low pressure, ear-like lobe which can be readily penetrated. Because it is a low-pressure area of the venous system, the risk of hemorrhage is low. In addition, the funnel-like shape of the right auricle facilitates catheter placement with minimal effort. That is, the catheter is naturally guided to the apex 112 of right auricle 108.

Figure 2:
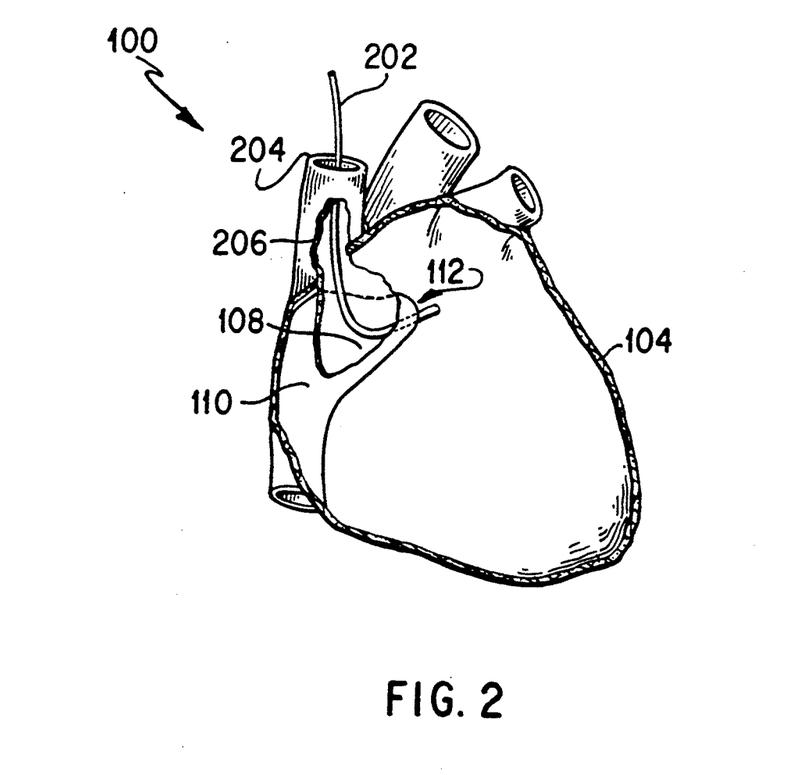
FIG. 2 is a diagram of a human heart as in FIG. 1 with pericardium 102 removed and a portion 206 of cardiac tissue cut away to show the route of a catheter inserted into the pericardial space via superior vena cava 204, right atrium 110, and right auricle 108.

Right auricle 108 may be accessed via conventional venae cavae routes. FIG. 2 illustrates entry of a catheter 202 into right atrium 110 via the superior vena cava 204. Pericardium 102 has been completely cut back in this figure such that only cut edge 104 is shown. A cut-away 206 shows passage of catheter 202 through superior vena cava 204, right atrium 110, and right auricle 108. A distal tip of catheter 202 is shown exiting right atrium 108 at apex 112.

Figure 3:
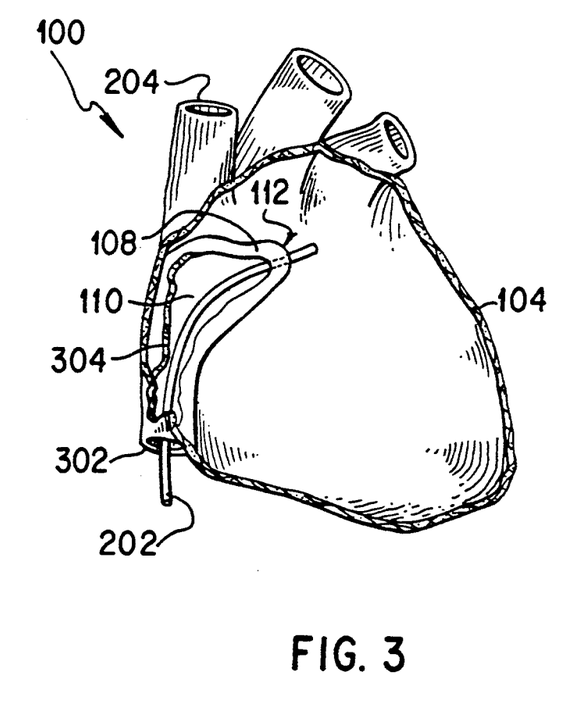
FIG. 3 is a diagram of a human heart as in FIG. 2 with pericardium 102 removed and a portion 304 of cardiac tissue cut away to show the route of a catheter inserted into the pericardial space via inferior vena cava 302, right atrium 110, and right auricle 108.

FIG. 3 illustrates entry of a catheter 202 into right atrium 110 via the inferior vena cava 302. As in FIG. 2, the pericardium 102 has been completely cut back such that only cut edge 104 is shown. A cut-away 304 shows passage of catheter 202 through inferior vena cava 302, right atrium 110, and right auricle 108. A distal tip of catheter 202 is shown exiting right atrium 108 at apex 112.

The method of the invention includes the following steps. Catheter 202 is maneuvered downstream through one of the venae cavae 204,302 to right atrium 110. Once inside right atrium 110, catheter 202 is passed into right auricle 108. The wall of right auricle 108 is pierced at apex 112, and the catheter is advanced into the pericardial space.

Figure 5:
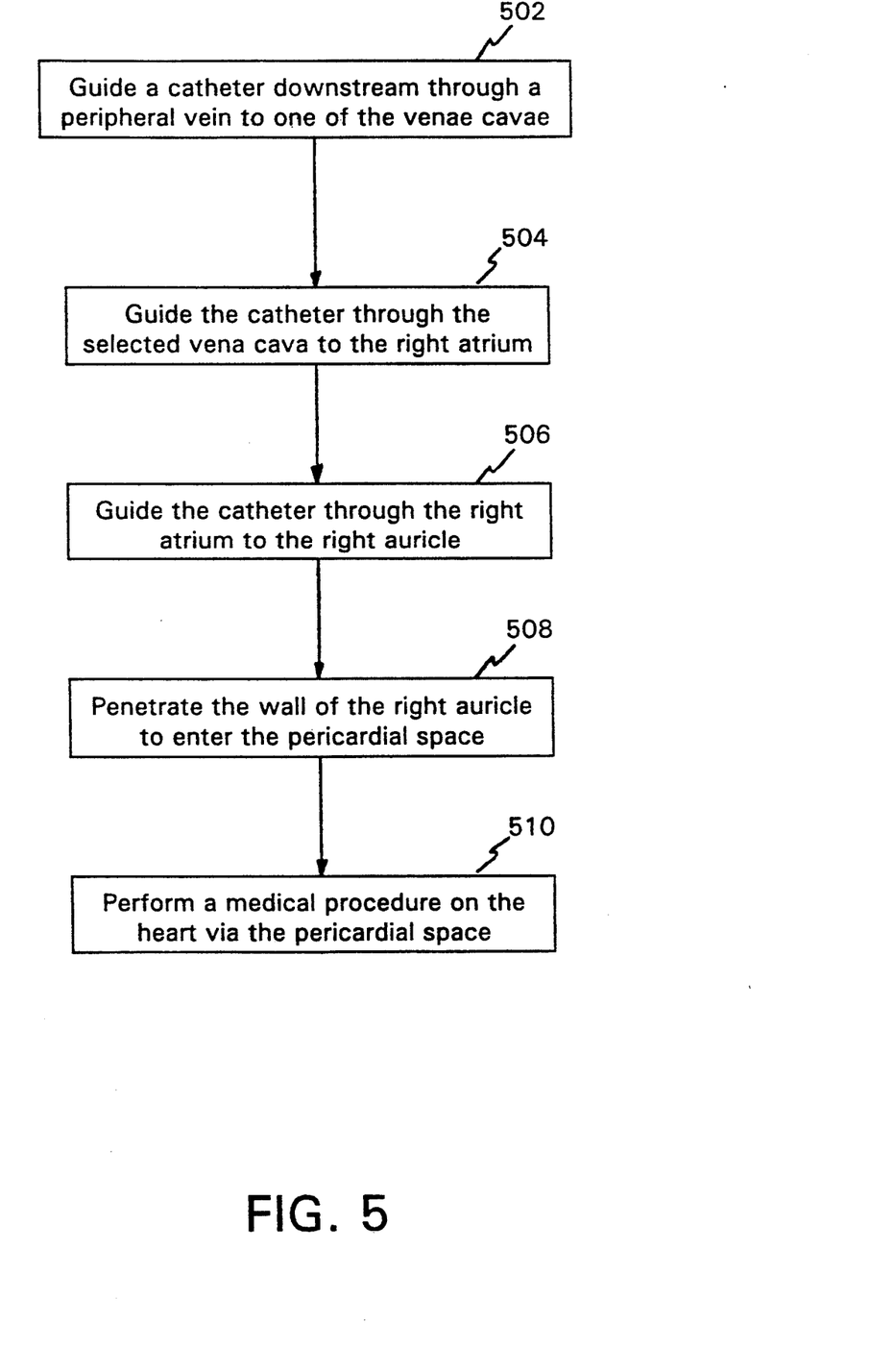
FIG. 5 is a flow chart illustrating the method of the invention.

This method is illustrated in the flow chart of FIG. 5. At step 502, a catheter is guided downstream through a peripheral vein to one of the venae cavae. The catheter is guided through the selected vena cava to the right atrium at step 504. At step 506, the catheter is passed through the right atrium to the right auricle. Finally, at step 508, the wall of the right auricle is pierced with the catheter to enter the pericardial space. Once in the pericardial space, a medical procedure may be performed on the heart as indicated by step 510.

Note that the wall of the right auricle may be pierced with the catheter itself, or with an instrument passed through the lumen of the catheter. Further, the catheter may be passed into the pericardial space through the opening in the wall of the auricle, or an instrument passed through the lumen of the catheter may be passed into the pericardial space. These details will depend on the procedure being performed and on the type of catheter being employed.

Figure 6:
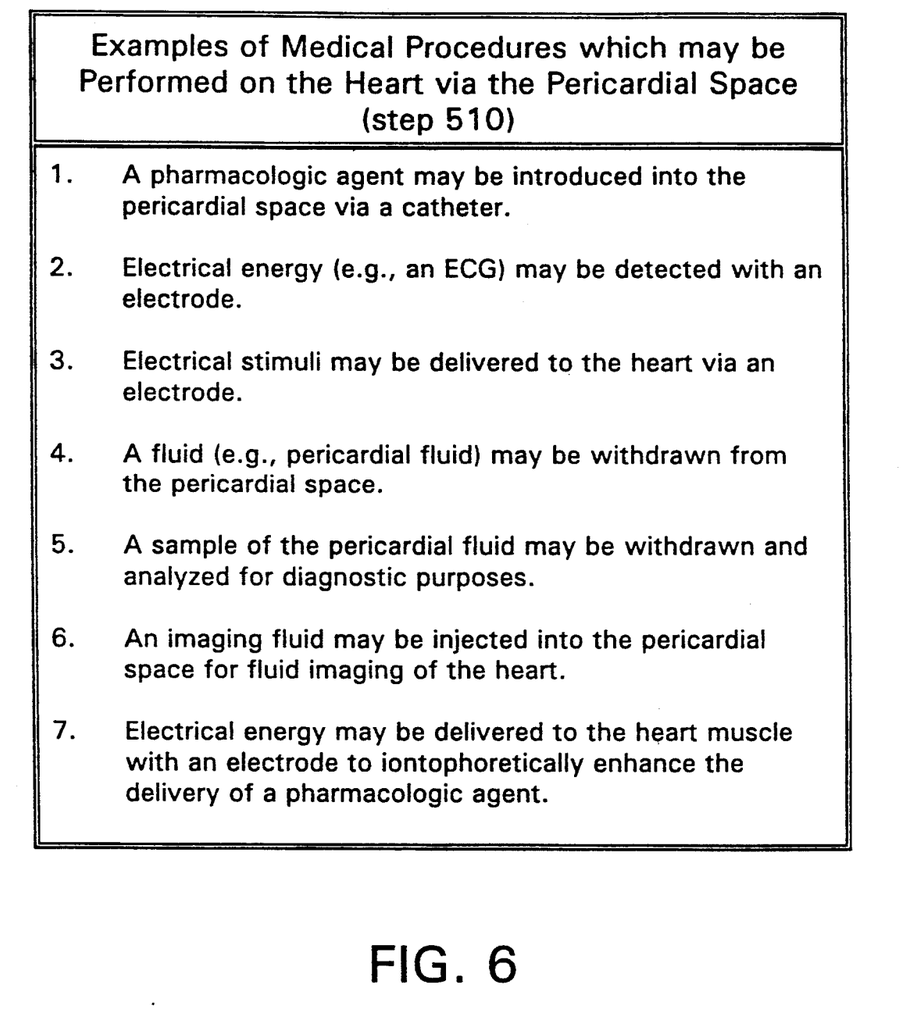
FIG. 6 is a table listing illustrative examples of medical procedures which may be performed on the heart via the pericardial space in accordance with the method set forth in FIG. 5.

FIG. 6 is a table listing examples of medical procedures which can be performed on the heart via the pericardial space in accordance with the present invention. Each of these procedures is described in detail below.

DELIVERY OF ELECTRICAL ENERGY TO THE HEART

The method of the present invention has utility for introducing electrodes to the surface of the heart within the pericardial space. Because the pericardial space is so small, electrodes guided into the space will be held in close contact with the cardiac muscle. These electrodes may be used to deliver an electrical charge for the purpose of cardiac pacing, cardioversion, or defibrillation.

For cardioversion and defibrillation, the inventor foresees the development of an unfurling "patch" electrode as discussed below. The point of exit from the right auricle allows a patch electrode to be readily positioned over the left ventricle, the area of most frequent cardiac injury. For chronic treatment, the patch electrode may be used in conjunction with implantable defibrillator/cardioverter units.

In addition to pacing, cardioversion, and defibrillation, electricity may be delivered to the heart according to the method of the invention for protection from arrhythmias and for iontophoretic delivery of drugs.

The heart can be protected from arrhythmias by delivering a relatively low-energy electrical charge to the heart during an interval of the cardiac cycle known as the "protective zone." For example, ventricular fibrillation can be prevented by delivering less than 1 joule of electrical energy to the heart during the protective zone. This is a significant discovery when one considers that 20-30 joules (delivered by internal means) are required for defibrillation. The protective zone corresponds to the portion of an ECG immediately following the vulnerable period of the T-wave. See, R. L. Verrier, et al., "Protective zone and the determination of vulnerability to ventricular fibrillation," *Am. J. Physiol.*, vol. 234, pp. H592-H596, 1978; and R. L. Verrier, et al., "Prevention of Ventricular Fibrillation by use of Low-Intensity Electrical Stimuli," *Annals of the New York Academy of Sciences*, 1982, pp. 355-370.

Iontophoresis involves enhancing the migration of a charged pharmacologic agent into a tissue by applying an external electric field. For example, by providing a mild electrical field over the heart muscle, the migration of electrically charged pharmacologic agents into the coronary arteries and heart tissue can be enhanced. The techniques of delivering drugs to the heart iontophoretically has been described in preliminary studies in anesthetized, thoracotomized dogs. See B. Avitall, et al., "Iontophoretic Delivery of Dobutamine: an Effective Method to Increase Contractility of Non-transmural Infarcts," [abstract], *J Am Coll Cardiol*, Vol. 17, 1991, p. 27A; and B. Avitall, et al., "Iontophoretic Transport of Procainamide and d-sotalol into Arrhythmogenic Myocardium: Efficacy in Ventricular Tachycardia Suppression," [abstract], *J Am Coll Cardiol*, Vol. 17, 1991, p. 39A.

ELECTROCARDIOGRAM SENSING

Electrodes positioned in contact with the cardiac muscles in the pericardial space can also be used for accurate electrocardiogram (ECG) sensing. A single electrode or a patch with an array of electrodes may be used. The latter could provide detailed information about excitation wavefronts to aid in diagnosis of tachyarrhythmias. An example of an application wherein precise ECG sensing is required is analysis of T-wave alternans. For more information on sensing and analysis of T-wave alternans, see B. Nearing, A. Huang, and R. Verrier, "Dynamic Tracking of Cardiac Vulnerability by Complex Demodulation of the T Wave," *Science*, Vol. 252, pp. 437-440, Apr. 19, 1991.

PERICARDIAL FLUID REMOVAL AND ANALYSIS

The pericardial space is filled with pericardial fluid. The pericardial fluid is in continuous contact with the cardiac muscles and coronary vessels. The present method may be used to remove pericardial fluid for pericardiocentesis or for analysis of the fluid.

Analysis of the constituents of the pericardial fluid may provide valuable evidence as to the condition of the cardiac muscles and coronary vessels. Diagnostic studies aided by the method of the invention include detection and diagnosis of diseases, infections, and hormonal abnormalities.

DELIVERY OF PHARMACOLOGIC AGENTS AND ENDOGENOUS SUBSTANCES TO THE HEART

The present invention further provides a safe method for the selective delivery of pharmacologic agents to the heart. As used herein, the term "pharmacologic agent" includes endogenous substances. When given through the conventional systemic routes (intravenous, oral, or intramuscular), these substances distribute throughout the body diluting their cardiac efficacy and creating the potential for developing adverse side effects elsewhere in the body. To overcome the dilution problem, higher doses/concentrations are used. This further exacerbates the potential for harmful side effects.

The pericardial fluid provides an excellent medium for delivery of pharmacologic agents to the cardiac muscles and coronary vessels without distribution to other organs. Among the clinically significant pharmacologic agents (i.e., drugs) which could advantageously be delivered to the heart via the pericardial fluid are those which improve cardiac contractility (e.g., digitalis drugs, adrenergic agonists, etc.), suppress arrhythmias (e.g., class I, II, III, and IV agents and specialized drugs such as amiodarone, which is particularly potent but has severe systemic side effects), dilate coronary arteries (e.g., nitroglycerin, calcium channel blockers, etc.), and lyse clots in the coronary circulation (e.g., thrombolytic agents such as streptokinase or tissue-type plasminogen activator (TPA)).

Examples of other pharmacologic agents which may be administered into the pericardial space include: agents to protect the heart pharmacologically from the toxic effects of drugs administered to the body generally for other diseases, such as cancer; antibiotics, steroidal and nonsteroidal medications for the treatment of certain pericardial diseases; and growth factors to promote angiogenesis or neovascularization of the heart. For additional information on angiogenesis, see J. Folkman, and M. Klagsbrun, "Angiogenic Factors," *Science*, Vol. 235, 1987, pp. 442-447; and S. W. Casscells, "Growth Factors in the Heart," *The Development and Regenerative Potential of Cardiac Muscle*, edited by J. O. Oberpillar, 1991, Harwood.

FLUID IMAGING

The method of the invention can also be used to introduce an imaging fluid, such as a radio-labelled or echo-sensitive dye, into the pericardial space for precision diagnostic imaging. An external monitoring device, such as a fluoroscope or ultrasonic imaging device, could then be used to produce an external image of the heart which would aid identification of the extent and location of cardiac injury.

CATHETERS

The method of the invention uses an intravenous catheter to access the pericardial space. Specialized catheters will be developed to optimize the many features and advantages of the invention. The optimal catheter for practicing the method of the invention, however, may have certain common characteristics. These include: self-sealing, sheathed, a radio-opaque portion to aid fluoroscopic positioning, a guide tube to aid positioning, and a distal flange to control the depth of entry into the pericardial space.

The catheter could be produced in various sizes to accommodate the variety of applications. For example, a very thin catheter could be used for drug infusion. A larger catheter would be required for electrical sensing and pacing, and for evacuation of pericardial fluid.

conventional cardiac catheters are available for delivery of electrical stimuli to the cardiac chambers but not to the epicardium.

The inventor contemplates developing a catheter which includes a retractable metallic "patch" electrode which may be inserted into the pericardial space according to the method of the invention. The patch electrode would be inserted in a retracted form and then unfurled once positioned in the pericardial space. Thus, an electrode having the surface area required for fibrillation could be implanted without thoracotomy.

The preferred trans-auricular catheterization technique involves penetration of the right auricle by first advancing a sheathed catheter to the apex of the right auricle and then piercing the thin wall with a rigid, tapered catheter extended out from the lumen of the sheath. Catheterization can be performed under fluoroscopic guidance, a routine method.

The catheter may be made from a material to inhibit or encourage fibrosis (tissue growth) depending on the application. For example, fibrous growth may be promoted for chronic catherterization in order to secure a catheter in position. Conversely, it is desirable to maintain easy removal of a catheter implanted for acute purposes such that fibrous growth may not be desirable.

In the example discussed below, a standard pediatric catheter was used to deliver pharmacologic agents to the pericardial space according to the method of the invention.

VENOUS ACCESS

The method of the invention allows the catheter to access the right auricle via the venae cavae 204,302. The venous routes for entering the venae cavae are now described with reference to FIG. 4.

Figure 4:
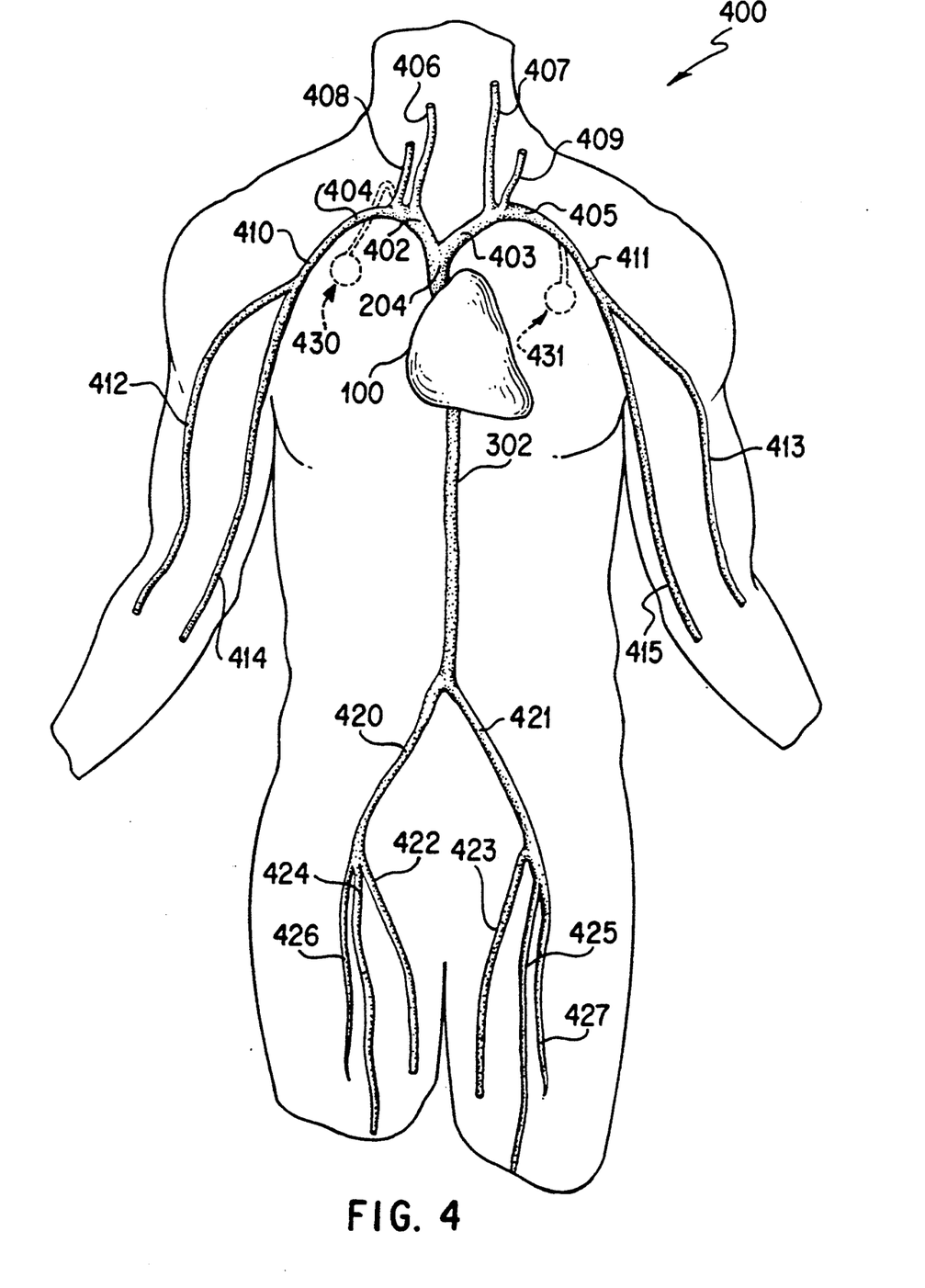
FIG. 4 is a diagram of a human body showing the heart and the major veins of the venous system.

Heart 100, along with several principal veins of the human body, are shown in a body 400 in FIG. 4. Superior vena cava 204 is a venous trunk which drains blood from the head, neck, upper extremities, and chest; and empties into right atrium 110 (not indicated in FIG. 4). Inferior vena cava 302 is a venous trunk which returns blood from the lower extremities and also empties into right atrium 110.

The venous system tends to be symmetrical, having a right side and a left side. Veins which empty into superior vena cava 204, right side and left side respectively, include the brachiocephalic veins 402,403; the subclavian veins 404,405; the internal jugular veins 406,407; the external jugular veins 408,409; the axillary veins 410,411; the cephalic veins 412,413; and the basilic veins 414,415.

Veins which empty into inferior vena cava 302, right side and left side respectively, include the external iliac veins 420,421; the great saphenous veins 422,423; the superficial femoral veins 424,425; and the deep femoral veins 426,427.

Any of these "upstream" veins can be used to access the venae cavae to practice the method of the present invention. These veins upstream from the venae cavae are herein referred to as "peripheral" veins.

ACUTE VERSUS CHRONIC CATHETERIZATION

For temporary access to the pericardial space for acute medical situations such as heart attack, pericardial edema, and heart failure, the catheter would normally be in place for a period of hours to days. In this case, the trans-auricular catheter may be passed through either the superior vena cava or the inferior vena cava via a peripheral vein (e.g., an axillary vein for the superior vena cava). These are standard routes in right heart catheterization. Other procedures made possible on a temporary basis include the delivery of drugs or thrombolytic or diagnostic imaging agents, pericardial fluid sampling, electrocardiographic testing, and pericardiocentesis.

For permanent access to the pericardial space (chronic catheterization), the trans-auricular catheter can be implanted through a subclavian vein 404,405 or external jugular vein 408,409; along with a subcutaneous drug infusion pump or defibrillator/cardioverter unit. The surgical procedure would be similar to those used for permanent cardiac pacemaker implants. This type of therapy would be used for chronic care situations requiring long term delivery of drugs or growth factors over months and years. Permanent access also provides the capability for electrical monitoring and stimulation (including pacing, protecting, cardioverting/defibrillating, iontophoretic drug delivery, etc.). Possible implantation sites for an infusion pump or defibrillator/cardioverter unit are indicated in FIG. 4 as 430 and 431.

Having now generally described the invention, the same will be better understood by reference to the specific example which is provided below for illustration purposes.

EXAMPLE

The method of the invention has been performed on a dog using a standard pediatric catheter. There was no noticeable bleeding from the myocardium upon puncturing of the wall of the right auricle. Minimal amounts of drugs were delivered into the pericardial sac according to the method of the invention with long-lasting effects. Two drugs were injected, namely isoproterenol and nitroglycerin. These agents resulted in remarkably and sustained effects on heart rate and coronary blood flow, respectively, at dosages well below (less than 10%) that required for standard intravenous injection.

Although the invention has been described and illustrated with a certain degree of particularity, it is understood that those skilled in the art will recognize a variety of applications and appropriate modifications within the spirit of the invention and the scope of the claims.

I claim:

1. A method for transvenously accessing the pericardial space between a heart and its pericardium in preparation for a medical procedure, said method comprising the following steps:
   (a) guiding a catheter downstream through one of the venae cavae to the right atrium;
   (b) guiding said catheter through the right atrium and into the right auricle; and
   (c) accessing the pericardial space with said catheter by penetrating through the wall of the right auricle.

2. The method of claim 1, wherein said one of the venae cavae is the superior vena cava.

3. The method of claim 2, wherein the catheter is introduced into the superior vena cava via a peripheral vein.

4. The method of claim 1, wherein said one of the venae cavae is the inferior vena cava.

5. The method of claim 4, wherein the catheter is introduced into the inferior vena cava via a peripheral vein.

6. A method for transvenously delivering a pharmacologic agent to the heart, said method comprising the following steps:
   (a) guiding a catheter downstream through one of the venae cavae to the right atrium;
   (b) guiding said catheter through the right atrium and into the right auricle;
   (c) accessing the pericardial space with said catheter by penetrating through the wall of the right auricle; and
   (d) introducing the pharmacologic agent into the pericardial space via said catheter.

7. The method of claim 6, further comprising the steps of:
   (e) passing an electrode through said catheter and into the pericardial space; and
   (f) delivering electrical energy to the heart muscle through said electrode to iontophoretically enhance the delivery of the pharmacologic agent.

8. A method for monitoring electrical activity of the heart, said method comprising the following steps:
   (a) guiding an electrode downstream through one of the venae cavae to the right atrium;
   (b) guiding said electrode through the right atrium and into the right auricle;
   (c) inserting said electrode into the pericardial space by penetrating through the wall of the right auricle; and
   (d) detecting electrical energy with said electrode.

9. A method for delivering electrical stimuli to the heart, said method comprising the following steps:
   (a) guiding an electrode downstream through one of the venae cavae to the right atrium;
   (b) guiding said electrode through the right atrium and into the right auricle;
   (c) inserting said electrode into the pericardial space by penetrating through the wall of the right auricle; and
   (d) delivering the electrical stimuli to the heart muscle via said electrode.

10. A method for performing pericardiocentesis, said method comprising the following steps:
    (a) guiding a catheter downstream through one of the venae cavae to the right atrium;
    (b) guiding said catheter through the right atrium and into the right auricle;
    (c) accessing the pericardial space with said catheter by penetrating through the wall of the right auricle; and
    (d) withdrawing a fluid from the pericardial space.

11. A diagnostic method for use with the heart, said method comprising the following steps:
    (a) guiding a catheter downstream through one of the venae cavae to the right atrium;
    (b) guiding said catheter through the right atrium and into the right auricle;
    (c) accessing the pericardial space with said catheter by penetrating through the wall of the right auricle;
    (d) sampling the pericardial fluid; and
    (e) analyzing said sample of the pericardial fluid for diagnostic purposes.

12. A method for diagnostic imaging of the heart, said method comprising the following steps:
    (a) guiding a catheter downstream through one of the venae cavae to the right atrium;
    (b) guiding said catheter through the right atrium and into the right auricle;
    (c) accessing the pericardial space with said catheter by penetrating through the wall of the right auricle;
    (d) injecting an imaging fluid into the pericardial space; and
    (e) monitoring said imaging fluid with an external sensing device.

13. A method for transvenously performing a medical procedure on a heart, the method comprising the following steps:
    (a) guiding a catheter downstream through one of the venae cavae to the right atrium;
    (b) guiding said catheter through the right atrium and into the right auricle;
    (c) accessing a pericardial space between the heart and its pericardium with said catheter by penetrating through the wall of the right auricle; and
    (d) performing the medical procedure on the heart via the pericardial space.

* * * * *